(12) United States Patent
Benton et al.

(10) Patent No.: US 7,407,800 B1
(45) Date of Patent: Aug. 5, 2008

(54) METHOD FOR THE ISOLATION OF INTACT MITOCHONDRIA FROM CELLS

(75) Inventors: Margaret Benton, Roscoe, IL (US); Reinere Ignacio, Rockford, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 360 days.

(21) Appl. No.: 11/098,848

(22) Filed: Apr. 5, 2005

Related U.S. Application Data

(63) Continuation-in-part of application No. 10/939,177, filed on Sep. 10, 2004.

(60) Provisional application No. 60/503,948, filed on Sep. 19, 2003.

(51) Int. Cl.
*C12N 1/00* (2006.01)
(52) U.S. Cl. .................................................. 435/317.1
(58) Field of Classification Search ................ 435/317.1
See application file for complete search history.

(56) References Cited

U.S. PATENT DOCUMENTS 5,645,986 A * 7/1997 West et al. ..................... 435/6

* cited by examiner

*Primary Examiner*—Sandra Saucier
*Assistant Examiner*—Susan Hanley

(57) ABSTRACT

Intact mitochondria is isolated from cells by swelling the cells, lysing the swollen cells using a mild detergent such as CHAPS to release the mitochondria, and then recovering the mitochondria.

12 Claims, No Drawings

METHOD FOR THE ISOLATION OF INTACT MITOCHONDRIA FROM CELLS

RELATED APPLICATION

This application is a Continuation-in Part of U.S. patent application Ser. No. 10/939,177, filed Sep. 10, 2004 which claims priority from Provisional Patent Application Ser. No. 60/503,948, filed Sep. 19, 2003.

FIELD OF INVENTION

The present invention relates to a new method for the isolation of intact mitochondria from cells, particularly from tissue and cultured mammalian cells.

BACKGROUND OF INVENTION

In the last decade, mitochondria research has undergone tremendous progress as new technologies and increased understanding have paved the way for new areas of investigation. Mitochondria are organelles that provide an energy source for cell processes. New disciplines have emerged studying the role of the mitochondria in apoptosis and in human diseases. An increase in awareness of the role that mitochondrial dysfunction plays in human disorders, such as diabetes, neurological diseases, heart disease, and a host of other new discoveries of human disorders necessitated the development of a more effective method to isolate intact mitochondria.

The currently employed method for the isolation of intact mitochondria is conventionally referred to as dounce homogenization. In this method, cells are mechanically lysed to release cell components by homogenization in a Polytron tissue tearer or Dounce tissue grinder. The extent of lysis can be measured visually by comparison under a microscope of the original intact cells with those after douncing. Douncing is customarily accomplished under physiological conditions in a buffer containing sugars to preserve organelle integrity which does not swell the cell in order to minimize damage to the organelle during lysis.

Subsequent to cell lysis, the homogenate containing the mitochondria suspended in the buffer is centrifuged at low speed to remove unbroken cells, cellular debris and nuclei from the suspension. The supernatant is then centrifuged at high speed, and the mitochondria, in pellet form, are recovered, rinsed with the sugar containing buffer, and used for applications, including studies as indicated above related to apoptosis, signal transduction and metabolism.

In practicing methods for recovering mitochondria, the manipulative steps are accomplished at a temperature of less than about 10° C. in order to preserve the activity of the organelle. It is also customary to finely mince the tissue prior to beginning the recovery process.

Known douncing methods have been used to isolate mitochondria from cultured cells and hard tissue (e.g. muscle or heart) and soft tissue (e.g. liver or kidney). The methods are applicable with respect to mammalian cells as well as those from other species.

SUMMARY OF INVENTION

In accordance with the present invention, intact mitochondria are isolated from cells using the general protocol involving lysing the cells to release the mitochondria, and then recovering the mitochondria in intact form. However, in accordance with the present invention, rather than using dounce homogenization for cell lysis, lysis is achieved using a mild detergent in a buffer at a physiological pH. To achieve cell lysis with the detergent, cells are first swelled in a hypotonic buffer (lower salt concentration than within cell to promote osmotic swelling within the cell) at a physiological pH followed by addition of detergent. After lysis with the detergent and before recovery of the intact mitochondria, conventionally accomplished by centrifugation, a buffer is added containing constituents to retard swelling of the Mitochondria and thereby maintain mitochondria integrity. Useful constituents for this purpose are non-reducing sugars such as mannitol, sorbitol, sucrose and the like. A chelator to remove metals which may also adversely affect the organelle are generally also present.

DESCRIPTION OF THE INVENTION

Low concentrations of mild detergents in the lysing solution are considered useful in practicing the present invention. Appropriate detergents and concentrations are selected so as to effect cell lysis of swollen cells without damaging the mitochondria. Those mild zwitterionic detergents referred to as CHAPS (3-[(3-Cholamidopropyl)dimethylammonio]-1-propanesulfonate) and CHAPSO (3-[(3-Cholamidopropyl) dimethylammonio]-2-hydroxy-1-propanesulfonate) are particularly useful. Useful concentrations, w/v, of detergent in the lysing buffer are about 0.05% to about 0.2%.

In keeping with this invention, prior to lysis, the cells are swollen by incubation in a hypotonic buffer at a physiological pH. The time of incubation in the buffer is important in realizing the final recovery of the mitochondria in intact form. The time must be sufficient to adequately swell the cells in order to achieve lysis on addition of the detergent, but not so long as to adversely affect the activity of the mitochondria within the cell due to swelling of the organelle itself. An incubation time about 2 minutes is generally useful. After lysis with the detergent, a buffer containing sugar or the like is added to the mixture to maintain organelle integrity and the mixture centrifuged to recover mitochondria in intact form.

An advantage associated with use of the reagent based lysing method of this invention is that an investigator can concurrently lyse multiple samples of cells. The dounce method, relying as it does on manual lysing, allows for only a single sample to be processed at a time. An additional advantage resides in the fact that organelle damage is minimized since non-mechanical lysis is used.

The present invention is applicable with respect to cultured cells as well as cells obtained directly from tissue. With respect to the latter, prior to swelling and lysing, it is desirable that assembled, minced tissue be disrupted to disassociate the individual components. To that end, mild grinding of the tissue sample, short of achieving lysis, can be employed. Treating the tissue, particularly hard tissue with a proteolytic enzyme, such as trypsin, can be used to promote the breakdown of the tissue's cellular structure and aid in subsequent lysing. When using an enzymatic treatment, enzymatic activity can be quenched by the addition of fatty-acid free bovine serum albumin (BSA) which also aids in removing fatty acids and assists is maintaining respiration for the mitochondria.

EXAMPLE I

About $2 \times 10^7$ of harvested cultured cells are centrifuged in a 2.0 ml microcentrifuge tube at ~850×g for 2 minutes. The supernatant is carefully removed and discarded. 800 μl of a hypotonic buffer, 20 mM HEPES, (N-(2-Hydroxyethyl)piperazine-N'-(2-ethanesulfonic acid)), pH 7.4, is added to the residual cells in the tube and the suspension vortexed at medium speed for five seconds, and then incubated on ice for exactly two minutes to swell the cells without compromising the integrity of the mitochondria.

Thereafter, the cells are lysed by adding to the tube 10 μl of a mixture of 20 mM HEPES, pH 7.4, and 8%, by weight, CHAPS (final CHAPS concentration of 0.1%), followed by vortexing at maximum speed for five seconds, and then incubating on ice for five minutes with vortexing at maximum speed every minute.

Subsequently, in order to minimize any swelling of the freed mitochondria, 800 μl of a buffer containing 20 mM HEPES, pH 7.4, 2 mM EGTA (ethylene glycol-bis(beta-aminoethyl ether)-N,N,N',N'-tetraacetic acid), 420 mM Mannitol, 140 mM Sucrose, and 0.03% microcide is added and the tube inverted several times to mix the contents. Mixing is then followed by centrifuging at 700×g for 10 minutes at 4° C. to remove cell debris, nuclei, and unbroken cells. The supernatant is then transferred to a new 2.0 ml tube and centrifuged at 12,000×g for 15 minutes at 4° C. to achieve a pellet of the mitochondria. In order to obtain a more purified fraction of mitochondria (less other organelle contamination), but with a sacrifice in yield, centrifuging can be accomplished at 3,000×g for 15 minutes. Final processing is accomplished by rinsing the pellet with 500 μl of the sugar containing buffer and centrifuging at 12,000×g for 5 minutes. The mitochondrial pellet is then maintained on ice until used.

EXAMPLE II

~50-200 mg of soft liver tissue are minced in PBS solution (0.1 M sodium phosphate, 0.15 M NaCl, pH 7.2) and ground using a Dounce homogenizer to disrupt the tissue associations, but short of cell lysis as seen under a microscope. The tissue homogenate is centrifuged at 1,000×g for three minutes at 4° C. The supernatant is carefully removed and discarded. 800 μl of 20 mM HEPES (N-(2-Hydroxyethyl)piperazine-N'-(2-ethanesulfonic acid)) buffer, pH 7.4, 4 mg/ml fatty-acid free BSA and 0.03% microcide is added to re-suspend the tissue pellet. The suspension is vortexed at medium speed for five seconds and then incubated on ice for exactly two minutes to avoid compromising the integrity of the mitochondria. Cell lysis is achieved by adding 10 μl of a mixture of 20 mM HEPES, pH 7.4, and 8%, by weight, CHAPS (3-[(3-Cholamidopropyl)dimethylammonio]-1-propanesulfonate). The final CHAPS concentration in the suspension is 0.1%. After which the sample is vortexed at maximum speed for five seconds and incubated on ice for five minutes. During the incubation, the sample is vortexed at maximum speed every minute.

Subsequently, 800 μl of sugar containing buffer containing 20 mM HEPES, pH 7.4, 2 mM EGTA (Ethylene glycol-bis(beta-aminoethyl ether)-N,N,N',N'-tetraacetic acid), 420 mM Mannitol, 140 mM Sucrose, 0.03% microcide is added and the tube inverted several times to mix. Mixing is then followed by centrifuging at 700×g for ten minutes at 4° C. to remove cell debris, nuclei, and unbroken cells. The supernatant is carefully transferred to a new 2 mL tube and centrifuged at 3,000×g for fifteen minutes at 4° C. to achieve a pellet of the mitochondria. This lower centrifugation speed than used in Example I helps reduce organelle contamination, i.e. lysosomes and peroxisomes, of the mitochondria fraction.

Final processing of the mitochondria sample is accomplished by rinsing the mitochondria pellet with 500 μl of the sugar containing buffer and centrifuging at 12,000×g for five minutes. The isolated mitochondria pellet is then maintained on ice until used.

EXAMPLE III

~50-200 mg of hard tissue (heart) are minced into smaller sizes in PBS solution containing 0.3 mg/ml of Trypsin and incubated on ice for three minutes. After incubation, the sample is centrifuged at 700×g for one minute at 4° C. The supernatant is then carefully discarded and the tissue pellet collected. Add 800 μl of PBS solution containing 4 mg/ml of BSA and grind the tissue sample using a Polytron or Dounce homogenizer to disrupt the tissue associations. Centrifuge the tissue homogenate at 1,000×g for three minutes at 4° C. The supernatant is carefully removed and discarded. 800 μl of 20 mM HEPES (N-(2-Hydroxyethyl)piperazine-N'-(2-ethanesulfonic acid)) buffer, pH 7.4, 4 mg/ml fatty-acid free BSA and 0.03% microcide is added to re-suspend the tissue pellet. The suspension is vortexed at medium speed for five seconds and then incubated on ice for exactly two minutes to avoid compromising the integrity of the mitochondria. Cell lysis is achieved by adding 10 μl of a mixture of 20 mM HEPES, pH 7.4, and 8%, by weight, CHAPS (3-[(3-Cholamidopropyl)dimethylammonio]-1-propanesulfonate). The final CHAPS concentration in the suspension is 0.1%. After which the sample is vortexed at maximum speed for five seconds and incubated on ice for five minutes. During the incubation, the sample will be vortexed at maximum speed every minute.

Subsequently, 800 μl of buffer containing 20 mM HEPES, pH 7.4, 2 mM EGTA (Ethylene glycol-bis(beta-aminoethyl ether)-N,N,N',N'-tetraacetic acid), 420 mM Mannitol, 140 mM Sucrose, 0.03% microcide is added and the tube inverted several times to mix. Mixing is then followed by centrifuging at 700×g for ten minutes at 4° C. to remove cell debris, nuclei, and unbroken cells. The supernatant is carefully transferred to a new 2 mL tube and centrifuged at 3,000×g for fifteen minutes at 4° C. to achieve a pellet of the mitochondria. This lower centrifugation speed will help reduce organelle contamination, i.e. lysosomes and peroxisomes, of the mitochondria fraction. However, a higher mitochondria yield could be achieved by centrifuging at 12,000×g for fifteen minutes.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While this invention is illustrated herein with respect to mammalian cells, it, as with dounce homogenization, is considered applicable to other cell species as well.

The following examples illustrate this invention:

The invention claimed is:

1. A method for isolating intact mitochondria from cells comprising the steps of: lysing, the cells and then recovering the mitochondria in intact form, wherein, prior to lysing, the cells are swelled in a hypotonic buffer at a physiological pH and lysing is achieved with a detergent in a buffer at a physiological pH, wherein the detergent is selected from the group consisting of 3-[(3-cholamidapropyl)dimethylammonio]-1-propanesulfonate, 3-[(3-cholamidapropyl)dimethylammonio]-2-hydroxy-1-propanesulfonate, and combinations thereof, and wherein the concentration of the detergent in the lysing solution effects cell lysis without damaging the mitochondria, thus resulting in intact mitochondria, and wherein the detergent concentration is from about 0.05% w/v to about 0.2% w/v.

2. The method of claim 1 wherein subsequent to lysing and prior to recovery of intact mitochondria, a non-reducing sugar containing buffer is added to the mixture containing the lysed cells in order to avoid swelling of the released mitochondria and maintain the integrity of the organelle.

3. The method of claim 1 wherein the detergent concentration is about 0.1% w/v.

4. The method of claim 1 wherein the detergent concentration is from about 0.05% w/v to about 0.1% w/v.

5. The method of claim 1 wherein the detergent concentration is from about 0.1% w/v to about 0.2% w/v.

6. The method of claim 2 wherein the non-reducing sugar is selected from the group consisting of mannitol, sorbitol, and sucrose, and combinations thereof.

7. The method of claim 1 wherein the cells are cultured cells or from a tissue.

8. The method of claim 7 wherein the cells are from a tissue and the tissue is processed prior to isolating intact mitochondria.

9. The method of claim 8 wherein the tissue is processed by at least one of mechanical disruption, enzymatic treatment, or combinations thereof.

10. The method of claim 9 wherein the process is enzymatic treatment and the enzymatic treatment is quenched by the addition of fatty-acid free bovine serum albumin (BSA).

11. The method of claim 1 wherein the steps are conducted at a temperature of less than 10° C.

12. The method of claim 1 wherein the hypotonic buffer is a N-(2-hydroxyethyl)piperazine-N'- (2-ethanesulfonic acid) (HEPES) buffer.

* * * * *